(12) United States Patent
Goodacre et al.

(10) Patent No.: US 7,148,222 B2
(45) Date of Patent: Dec. 12, 2006

(54) SUBSTITUTED PYRIDO-PYRIDAZINE DERIVATIVES WHICH ENHANCE COGNITION VIA THE GABA-$_A$ RECEPTORS

(75) Inventors: Simon Charles Goodacre, Benington (GB); David James Hallett, Watford (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/531,517

(22) PCT Filed: Oct. 29, 2003

(86) PCT No.: PCT/GB03/04677

§ 371 (c)(1),
(2), (4) Date: Apr. 15, 2005

(87) PCT Pub. No.: WO2004/039802

PCT Pub. Date: May 13, 2004

(65) Prior Publication Data

US 2006/0041125 A1    Feb. 23, 2006

(30) Foreign Application Priority Data

Nov. 1, 2002    (GB) .................................. 0225501.6

(51) Int. Cl.
*C07D 471/04*    (2006.01)
*A61K 31/5025*    (2006.01)

(52) U.S. Cl. ...................................... 514/248; 544/236

(58) Field of Classification Search ................ 544/236; 514/248
See application file for complete search history.

(56) References Cited

FOREIGN PATENT DOCUMENTS

| WO | WO 01 90108 | 11/2001 |
|----|-------------|---------|
| WO | WO 03 006464 | 1/2003 |

*Primary Examiner*—Kahsay Habte
(74) *Attorney, Agent, or Firm*—J. Eric Thies; Melvin Winokur

(57) ABSTRACT

The present invention discloses a compound of formula 1, or a pharmaceutically acceptable salt thereof: wherein $X^1$ represents hydrogen, halogen, $C_{1-6}$ alkyl, trifluoromethyl or $C_{1-6}$ alkoxy; $X^2$ represents hydrogen or halogen; Y represents a chemical bond, an oxygen atom, or a —NH— linkage; Z represents an optionally substituted aryl or heteroaryl group; $R^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, NR$^a$R$^b$, —NR$^a$COR$^b$, —NR$^a$CO$_2$R$^b$, —COR$^a$, —CO$_2$R$^a$, —CONR$^a$R$^b$ or —CR$^a$&=NOR$^b$; and Ra and Rb independently represent hydrogen, hydrocarbon or a heterocyclic group; a pharmaceutical composition comprising it; its use in a method of treatment; use of it to manufacture a medicament; and a method of using it to prevent or treat anxiety, convulsions or cognitive disorders.

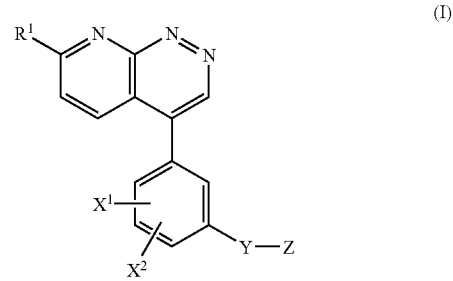

8 Claims, No Drawings

SUBSTITUTED PYRIDO-PYRIDAZINE DERIVATIVES WHICH ENHANCE COGNITION VIA THE GABA-A RECEPTORS

CROSS REFERENCE TO RELATED APPLICATIONS

This application is a U.S. National Phase application under 35 U.S.C. § 371 of PCT Application No. PCT/GB2003/004677, filed Oct. 29, 2003, which claims priority under 35 U.S.C. § 119 from GB Application No. 0225501.6, filed Nov. 1, 2002.

The present invention relates to a class of substituted pyrido-pyridazine derivatives and to their use in therapy. More particularly, this invention is concerned with pyrido[2,3-c]pyridazine analogues which are substituted in the 4-position by a substituted phenyl ring. These compounds are ligands for $GABA_A$ receptors and are therefore useful in the therapy of adverse neurological disorders.

The technical background to the present invention is disclosed on pages 1–4 of WO-A-02074773.

The present invention provides a class of pyrido-pyridazine derivatives which possess desirable binding properties at various $GABA_A$ receptor subtypes. The compounds in accordance with the present invention have good affinity as ligands for the α2 and/or α3 and/or α5 subunit of the human $GABA_A$ receptor. The compounds of this invention may interact more favourably with the α2 and/or α3 subunit than with the α1 subunit; and/or may interact more favourably with the α5 subunit than with the α1 subunit.

The compounds of the present invention are $GABA_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a pharmaceutically acceptable salt thereof:

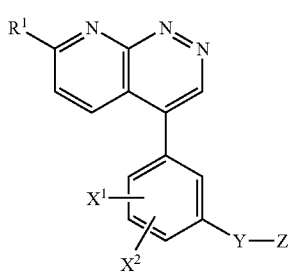

(I)

wherein $X^1$ represents hydrogen, halogen, $C_{1-6}$ alkyl, trifluoromethyl or $C_{1-6}$ alkoxy;

$X^2$ represents hydrogen or halogen;

Y represents a chemical bond, an oxygen atom, or a —NH— linkage;

Z represents an optionally substituted aryl or heteroaryl group;

$R^1$ represents hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$ or —$CR^a$=$NOR^b$; and $R^a$ and $R^b$ independently represent hydrogen, hydrocarbon or a heterocyclic group.

The aryl or heteroaryl group Z in the compounds of formula I above may be unsubstituted, or substituted by one or more substituents. Typically, the group Z will be unsubstituted, or substituted by one or two substituents. Suitably, the group Z is unsubstituted or monosubstituted. Typical substituents on the group Z include halogen, cyano, nitro, $C_{1-6}$ alkyl, hydroxy, $C_{1-6}$ alkoxy, oxy, $C_{1-6}$ alkylsulphonyl, amino, aminocarbonyl, formyl, $C_{2-6}$ alkoxycarbonyl and —$CR^a$=$NOR^b$, wherein $R^a$ and $R^b$ are as defined above.

Information about salts useful in the present invention, definitions of the term "hydrocarbon" and the expression "a heterocyclic group", suitable alkyl, alkenyl, alkynyl and cycloalkyl groups, typical $C_{3-7}$cycloalkyl($C_{1-6}$)alkyl groups, particular indanyl, aryl and aryl($C_{1-6}$)alkyl groups, suitable heterocycloalkyl and heteroaryl groups, the expression "hetero($C_{1-6}$)alkyl", optional substituents on hydrocarbon and heterocyclic groups, the term "halogen" and asymmetric compounds can be found on pages 6 to 9 of WO-A-02074773.

Suitable values for the $X^1$ substituent include hydrogen, fluoro, chloro, methyl, trifluoromethyl and methoxy; in particular hydrogen or fluoro; and especially fluoro.

Typical values of $X^2$ include hydrogen and fluoro, especially hydrogen.

In a preferred embodiment, Y represents a chemical bond.

In another embodiment, Y represents an oxygen atom.

In a further embodiment, Y represents a —NH— linkage.

Selected values for the substituent Z include phenyl, pyridinyl, pyridazinyl, pyrimidinyl, pyrazinyl, furyl, thienyl, oxazolyl, isoxazolyl, thiazolyl, isothiazolyl, pyrrolyl, pyrazolyl, imidazolyl, oxadiazolyl, thiadiazolyl, triazolyl and tetrazolyl, any of which groups may be optionally substituted by one or more substituents.

In one favoured embodiment, Z represents an optionally substituted phenyl group, in particular monosubstituted or disubstituted phenyl. In another favoured embodiment, Z represents optionally substituted pyridinyl, especially unsubstituted, monosubstituted or disubstituted pyridin-2-yl, pyridin-3-yl or pyridin-4-yl.

Examples of suitable substituents on the group Z include fluoro, chloro, cyano, nitro, methyl, hydroxy, methoxy, oxy, methanesulphonyl, amino, aminocarbonyl, formyl, methoxycarbonyl and —CH=NOH.

Examples of particular substituents on the group Z include fluoro and cyano, especially cyano.

Detailed values of Z include cyanophenyl, (cyano)(fluoro)phenyl, (chloro)(cyano)phenyl, nitrophenyl, methoxyphenyl, methanesulphonyl-phenyl, pyridinyl, fluoro-pyridinyl, difluoro-pyridinyl, (amino)(chloro)pyridinyl, cyano-pyridinyl, methyl-pyridinyl, hydroxy-pyridinyl, methoxy-pyridinyl, oxy-pyridinyl, aminocarbonyl-pyridinyl, pyridazinyl, pyrimidinyl, pyrazinyl, cyano-thienyl, aminocarbonyl-thienyl, formyl-thienyl, methoxycarbonyl-thienyl, thienyl—CH=NOH, thiazolyl, isothiazolyl, pyrrolyl, pyrazolyl, imidazolyl, triazolyl and methyl-tetrazolyl.

Specific values of Z include cyanophenyl, (cyano)(fluoro)phenyl, pyridinyl, difluoro-pyridinyl and cyano-pyridinyl.

In one embodiment, Z represents cyanophenyl, especially 2-cyanophenyl.

Typically, $R^1$ represents hydrogen, hydrocarbon, a heterocyclic group, halogen, cyano, trifluoromethyl, —$COR^a$, —$CO_2R^a$ or —$CR^a$=$NOR^b$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Suitable values of $R^1$ include hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$ alkoxycarbonyl($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl and —$CR^a$=$NOR^b$, in which $R^a$ and $R^b$ are as defined above.

Representative values of $R^1$ include $C_{1-6}$ alkyl, halo($C_{1-6}$)alkyl, hydroxy($C_{1-6}$)alkyl and trifluoromethyl.

Individual values of $R^1$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —$CR^2$=$NOR^3$, in which $R^2$ represents hydrogen or methyl, and $R^3$ represents hydrogen, hydroxyethyl or dimethylaminoethyl.

In a favoured embodiment, $R^1$ represents 2-hydroxyprop-2-yl. In another embodiment, $R^1$ represents 2-fluoroprop-2-yl. In an additional embodiment, $R^1$ represents trifluoromethyl. In a further embodiment, $R^1$ represents methyl.

Suitably, $R^2$ is hydrogen.

Suitably, $R^3$ represents hydrogen or dimethylaminoethyl, especially hydrogen.

A particular sub-class of compounds according to the invention is represented by the compounds of formula IIA, and pharmaceutically acceptable salts thereof.

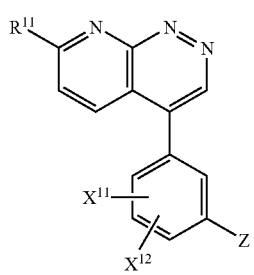

(IIA)

wherein

Z is as defined above;

$X^{11}$ represents hydrogen, fluoro, chloro, methyl, trifluoromethyl or methoxy;

$X^{12}$ represents hydrogen or fluoro;

$R^{11}$ represents hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$ alkoxycarbonyl($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl or —$CR^4$=$NOR^5$;

$R^4$ represents hydrogen or $C_{1-6}$ alkyl; and $R^5$ represents hydrogen, $C_{1-6}$ alkyl, hydroxy($C_{1-6}$)alkyl or di($C_{1-6}$)alkylamino($C_{1-6}$)alkyl.

Suitable values of $X^{11}$ include hydrogen and fluoro, especially fluoro.

In a favoured embodiment, $X^{12}$ represents hydrogen. In another embodiment, $X^{12}$ represents fluoro.

Suitably, $R^4$ represents hydrogen or methyl, especially hydrogen.

Suitably, $R^5$ represents hydrogen, methyl, ethyl, hydroxyethyl or dimethylaminoethyl. Particular values of $R^5$ include hydrogen, hydroxyethyl and dimethylaminoethyl. Typically, $R^5$ represents hydrogen or dimethylaminoethyl, especially hydrogen.

Where $R^{11}$ represents heteroaryl, this group is suitably pyridinyl, furyl, thienyl or oxazolyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents hetero*l($C_{1-6}$)alkyl, this group is suitably imidazolylmethyl or triazolylmethyl.

Representative values of $R^{11}$ include $C_{1-6}$ alkyl, hydroxy($C_{1-6}$)alkyl, fluoro($C_{1-6}$)alkyl and trifluoromethyl.

Individual values of $R^{11}$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tertbutyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —$CR^2$=$NOR^3$, in which $R^2$ and $R^3$ are as defined above.

In a favoured embodiment, $R^{11}$ represents 2-hydroxyprop-2-yl. In another embodiment, $R^{11}$ represents 2-fluoroprop-2-yl. In an additional embodiment, $R^{11}$ represents trifluoromethyl. In a further embodiment, $R^{11}$ represents methyl.

One representative subset of the compounds of formula IIA above is represented by the compounds of formula IIB, and pharmaceutically acceptable salts thereof:

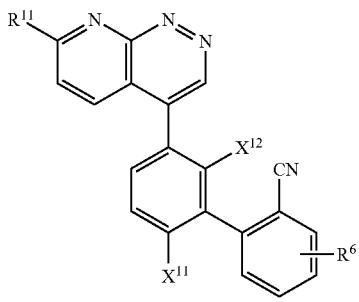

(IIB)

wherein $X^{11}$, $X^{12}$ and $R^{11}$ are as defined above; and
$R^6$ represents hydrogen or fluoro.

In one embodiment, $R^6$ is hydrogen.

In another embodiment, $R^6$ is fluoro, in which case the fluorine atom $R^6$ is favourably attached to the phenyl ring at the 4-, 5- or 6-position (relative to the cyano group at position 2).

Another representative subset of the compounds of formula IIA above is represented by the compounds of formula IIC, and pharmaceutically acceptable salts thereof:

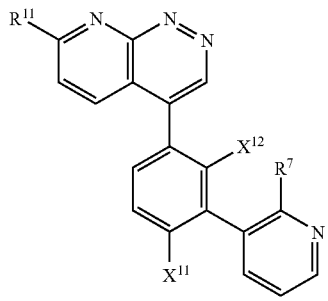

(IIC)

wherein $X^{11}$, $X^{12}$ and $R^{11}$ are as defined above; and
$R^7$ represents hydrogen, fluoro, cyano or methyl.

In one embodiment, $R^7$ is hydrogen.

In an additional embodiment, $R^7$ is fluoro.

In another embodiment, $R^7$ is cyano.

In a further embodiment, $R^7$ is methyl.

A further representative subset of the compounds of formula IIA above is represented by the compounds of formula IID, and pharmaceutically acceptable salts thereof:

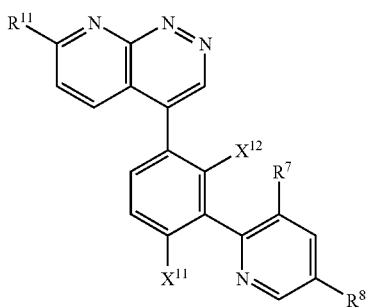

(IID)

wherein $X^{11}$, $X^{12}$, $R^7$ and $R^{11}$ are as defined above; and
$R^8$ represents hydrogen or fluoro.

Suitably, $R^8$ represents hydrogen.

In another embodiment, $R^8$ represents fluoro.

Specific compounds within the scope of the present invention include:
2'-fluoro-5'-(7-trifluoromethylpyrido[2,3-c]pyridazin-4-yl)biphenyl-2-carbonitrile;

and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

Details of the binding affinity, functional efficacy and anxiolytic and anticonvulsant activity of the present compounds can be found on pages 27 and 28 of WO-A-02074773.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

Details of pharmaceutical formulations of use in the present invention can be found on pages 28 and 29 of WO-A-02074773.

Unit dosage forms of the present invention contain from 0.1 to about 500 mg of the active ingredient of the present invention. Typical unit dosage forms contain from 1 to 100 mg, for example 1, 2, 5, 10, 25, 50 or 100 mg, of the active ingredient.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

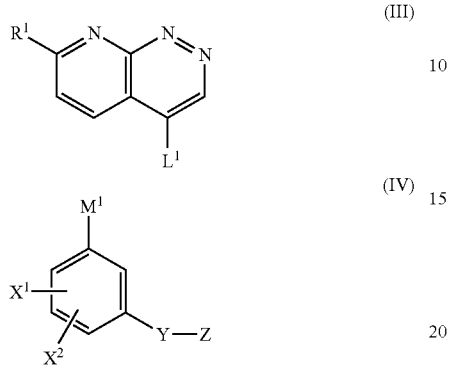

(III)

(IV)

wherein $X^1$, $X_2$, Y, Z and $R^1$ are as defined above, $L^1$ represents a suitable leaving group, and $M^1$ represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. chloro or bromo.

The transition metal catalyst of use in the reaction between compounds III and IV is suitably tetrakis(triphenylphosphine)palladium(0). The reaction is conveniently carried out at an elevated temperature in a solvent such as N,N-dimethylacetamide, 1,4-dioxane or 1,2-dimethoxyethane, advantageously in the presence of potassium phosphate, copper(I),iodide, sodium carbonate or cesium carbonate. Alternatively, the transition metal catalyst employed may be dichloro[1,1'-bis(diphenylphosphino)ferrocene]palladium(II), in which case the reaction is conveniently effected at an elevated temperature in a solvent such as N,N-dimethylformamide, advantageously in the presence of potassium phosphate.

In an alternative procedure, the compounds according to the present invention may be prepared by a process which comprises reacting a compound of formula V with a compound of formula VI:

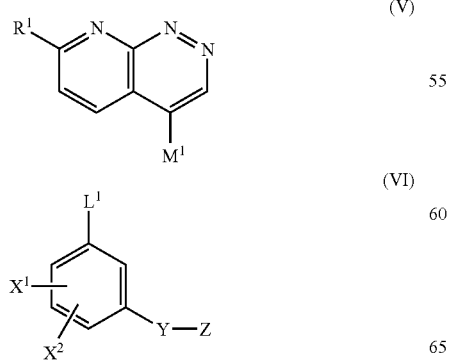

(V)

(VI)

wherein $X^1$, $X^2$, Y, Z, $R^1$, $L^1$ and $M^1$ are as defined above; in the presence of a transition metal catalyst; under conditions analogous to those described above for the reaction between compounds III and IV.

In another procedure, the compounds according to the present invention in which Y represents a chemical bond may be prepared by a process which comprises reacting a compound of formula VII with a compound of formula VIII:

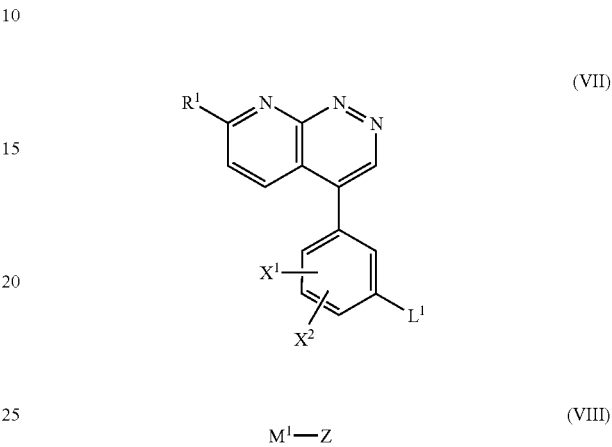

(VII)

(VIII)

wherein $X^1$, $X^2$, Z, $R^1$, $L^1$ and $M^1$ are as defined above; in the presence of a transition metal catalyst; under conditions analogous to those described above for the reaction between compounds III and IV.

In the compounds of formula VI and VII above, the leaving group $L^1$ is typically trifluoromethanesulfonyloxy (triflyloxy); or a halogen atom, e.g. bromo.

Alternatively, the compounds according to the present invention in which Y represents a chemical bond may be prepared by a process which comprises reacting a compound of formula IX with a compound of formula X:

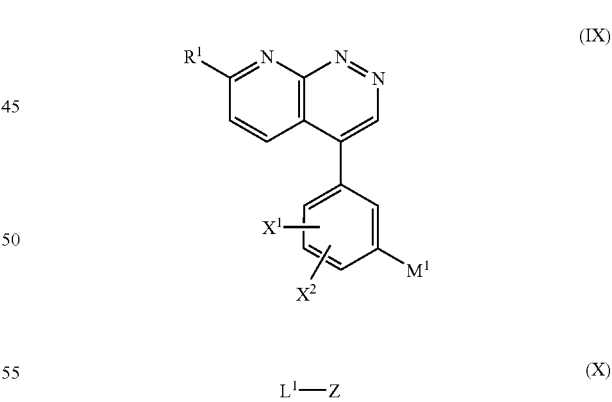

(IX)

(X)

wherein $X^1$, $X^2$, Z, $R^1$, $L^1$ and $M^1$ are as defined above; in the presence of a transition metal catalyst; under conditions analogous to those described above for the reaction between compounds III and IV.

In an additional procedure, the compounds according to the present invention in which Y represents an oxygen atom may be prepared by a process which comprises reacting a compound of formula X as defined above with a compound of formula XI:

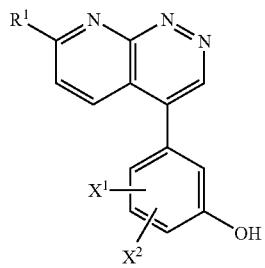

(XI)

wherein $X^1$, $X^2$ and $R^1$ are as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH— linkage may be prepared by a process which comprises reacting a compound of formula X as defined above with a compound of formula XII:

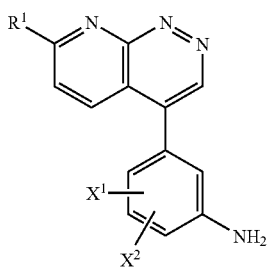

(XII)

wherein $X^1$, $X^2$ and $R^1$ are as defined above.

In relation to the reaction between compounds X and XII, the leaving group $L^1$ in the compounds of formula X may suitably represent fluoro.

The reaction between compounds X and XII is conveniently carried out by heating the reactants, typically at a temperature in the region of 120° C., in a solvent such as N,N-dimethylformamide.

Where $M^1$ in the intermediates of formula IV and IX above represents a boronic acid moiety —B(OH)$_2$ or a cyclic ester thereof formed with pinacol or neopentyl glycol, the relevant compound IV or IX may be prepared by reacting bis(pinacolato)diboron or bis(neopentyl glycolato)diborane respectively with a compound of formula VI or VII as defined above; in the presence of a transition metal catalyst.

The transition metal catalyst of use in the reaction between bis(pinacolato)diboron or bis(neopentyl glycolato) diborane and compound VI or VII is suitably dichloro[1,1'-bis(diphenylphosphino)ferrocene]palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

Where $L^1$ in the intermediates of formula VII above represents triflyloxy, the relevant compound VII may be prepared by reacting the appropriate compound of formula XI as defined above with triflic anhydride, typically in the presence of pyridine. Analogous conditions may be utilised for preparing a compound of formula VI wherein $L^1$ represents triflyloxy from the corresponding hydroxy precursor.

The intermediates of formula XI above may suitably be prepared from the appropriate methoxy-substituted precursor of formula XIII:

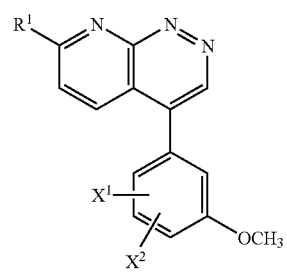

(XIII)

wherein $X^1$, $X^2$ and $R^1$ are as defined above; by treatment with boron tribromide, typically in chloroform or dichloromethane; or with hydrogen bromide, typically in acetic acid at reflux.

The intermediates of formula XI and XIII above may be prepared by reacting a compound of formula III as defined above with the appropriate compound of formula XIV:

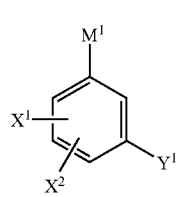

(XIV)

wherein $X^1$, $X^2$ and $M^1$ are as defined above, and $Y^1$ represents amino or methoxy; in the presence of a transition metal catalyst; under conditions analogous to those described above for the reaction between compounds III and IV. In particular, the transition metal catalyst of use in the reaction between compounds III and XIV is suitably tetrakis(triphenylphosphine)palladium(0), in which case the reaction is conveniently carried out at an elevated temperature in a solvent such as aqueous 1,2-dimethoxyethane, advantageously in the presence of sodium carbonate.

Where $M^1$ in the intermediates of formula V above represents —Sn(Alk)$_3$ and Alk is as defined above, this compound may be prepared by reacting a compound of formula III as defined above with a reagent of formula (Alk)$_3$Sn-Hal, in which Hal represents a halogen atom, typically chloro. The reaction is conveniently effected by treating compound III with isopropylmagnesium chloride, typically in a solvent such as tetrahydrofuran, with subsequent addition of the stannyl reagent (Alk)$_3$Sn-Hal.

Where $L^1$ in the intermediates of formula III above represents chloro, this compound may be prepared by chlorination of the corresponding compound of formula XV:

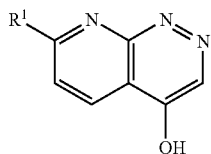

(XV)

wherein $R^1$ is as defined above; typically by treatment with phosphorus oxychloride in the presence of pyridine and a solvent such as chlorobenzene.

The intermediates of formula XV may conveniently be prepared by the sequence of steps depicted in the following reaction scheme:

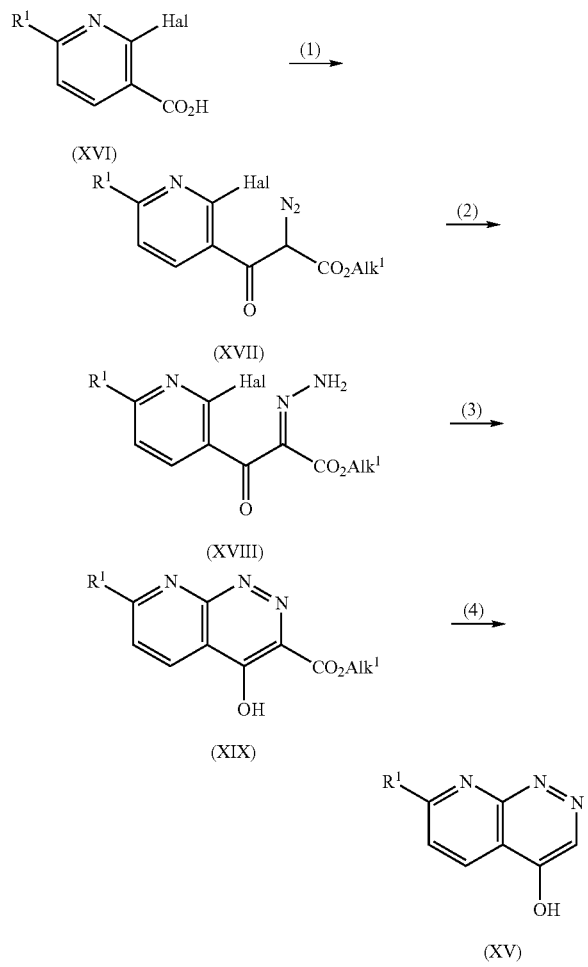

wherein Hal is as defined above, and $Alk^1$ represents $C_{1-6}$ alkyl, e.g. ethyl.

In step (1), the carboxy group of the halopyridine XVI is converted, by treatment with thionyl chloride, into an acid chloride moiety —COCl; the resulting molecule is then reacted with an alkyl azoacetate, e.g. ethyl azoacetate, to afford intermediate XVII. This is then treated, in step (2), with triphenylphosphine, typically in chloroform and isopropyl ether, to give intermediate XVIII, which is cyclised, in step (3), suitably by heating in Dowtherm to a temperature in the region of 200° C. In step (4), the intermediate of formula XIX thereby obtained is saponified by treatment with potassium hydroxide, then decarboxylated, typically by beating under reflux in Dowtherm, to provide the desired intermediate of formula XV.

In a yet further procedure, the compounds according to the present invention wherein $R^1$ represents an aryl or heteroaryl moiety may be prepared by a process which comprises reacting a compound of formula XX with a compound of formula XXI:

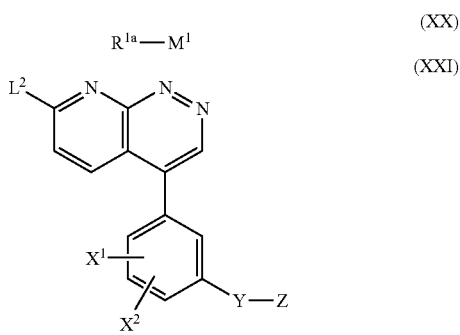

wherein $X^1$, $X^2$, Y, Z and $M^1$ are as defined above, $R^{1a}$ represents an aryl or heteroaryl moiety, and $L^2$ represents a suitable leaving group; in the presence of a transition metal catalyst.

The leaving group $L^2$ is typically a halogen atom, e.g. chloro.

The transition metal catalyst of use in the reaction between compounds XX and XXI is suitably tetrakis(triphenylphosphine)palladium(0), in which case the reaction is conveniently effected at an elevated temperature in a solvent such as N,N-dimethylacetamide, typically in the presence of potassium phosphate or in the presence of lithium chloride and copper(I) iodide. Alternatively, the transition metal catalyst may suitably be tris(dibenzylideneacetone)dipalladium(0), in which case the reaction is conveniently effected at an elevated temperature in a solvent such as 1,4-dioxane, typically in the presence of tri-tert-butylphosphine and cesium carbonate.

Where $L^2$ in the compounds of formula XXI above represents a halogen atom, these compounds correspond to compounds of formula I as defined above wherein $R^1$ represents halogen, and they may therefore be prepared by any of the methods described above for the preparation of the compounds according to the invention.

The compounds according to the invention in which Y represents a chemical bond and Z represents pyrrol-1-yl may be prepared by reacting a compound of formula XII as defined above with 2,5-dimethoxy-tetrahydrofuran. The reaction is conveniently accomplished at an elevated temperature in a solvent such as acetic acid.

Where they are not commercially available, the starting materials of formula VIII, X, XIV, XVI and XX may be prepared by methods analogous to those described in the accompanying Examples, or by standard methods well known from the art.

Standard interconversions of compounds of formula I are described on pages 40–42 of WO-A-02074773.

Standard methods for purifying, resolving and protecting compounds are described on pages 42 to 43 of WO-A-02074773.

Assays for testing the present compounds are described on pages 43 and 44 of WO-A-02074773.

The compound of the accompanying Example was tested in the above assay, and was found to possess a $K_i$ value for displacement of [$^3$H]-flumazenil from the α2 and/or α3 and/or α5 subunit of the human GABA$_A$ receptor of 100 nM or less.

The following Example illustrates the preparation of compounds according to the invention.

EXAMPLE 1

2'-Fluoro-5'-(7-trifluoromethylpyrido[2,3-c]pyridazin-4-yl)biphenyl-2-carbonitrile 2-Chloro-6-trifluoromethylnicotinic acid (10.0 g, 44.3 mmol) was suspended in thionyl chloride (85 ml) and heated under reflux for 2 h. The mixture was allowed to cool to ambient temperature, the solvent was removed in vacuo, toluene (50 ml) was added and the solution concentrated to afford a brown residue. This residue was cooled to −10° C. before ethyl diazoacetate (12.7 g, 110 mmol) was added dropwise over 30 min (maintaining the internal temperature below −5° C.). On complete addition the mixture was allowed to stir at 0° C. for 1 h then heated at 55° C. for 18 h. The mixture was allowed to cool to ambient temperature then evaporated. The residue was purified by dry flash chromatography on silica eluting with isohexane on a gradient of ethyl acetate (10–30%). Collecting the appropriate fractions gave 3-(2-chloro-6-trifluoromethyl-pyridin-3-yl)-2-diazo-3-oxo-propionic acid ethyl ester (13.7 g, 96%) as a yellow oil: $δ_H$ (400 MHz, CDCl$_3$) 1.17 (3H, t, J7), 4.15 (2H, q, J7), 7.68 (1H, d, J8), 7.78 (1H, d, J8), CHN$_2$ absent.

The above product (13.7 g, 42.6 mmol) was dissolved in chloroform (70 ml) and isopropyl ether (70 ml) and triphenylphosphine (13.4 g, 51.1 mmol) was added portionwise over. 5 min. The mixture was stirred at ambient temperature for 66 h, water (3 ml) was added followed by silica and this mixture was then concentrated to give a free-flowing powder. Purification by dry flash chromatography on silica eluting with isohexane on a gradient of ethyl acetate (10–50%) gave a yellow oil, which crystallised on standing. The solid was dissolved in xylenes (150 ml) and heated at 140° C. for 15 h. The mixture was allowed to cool to ambient temperature and the resulting solid collected by filtration. This was washed with isohexane (100 ml) and dried to afford 4-hydroxy-7-trifluoromethylpyrido[2,3-c]pyridazine-3-carboxylic acid ethyl ester (5.37 g, 44%) as a white solid: $δ_H$ (400 MHz, CDCl$_3$) 1.45 (3H, t, J7), 4.54 (2H, q, J 7), 7.79 (1H, d, J8), 8.85 (1H, d, J8), 10.90 (1H, s).

A suspension of the above product (2.0 g, 7.0 mmol) and potassium hydroxide (2.3 g, 41.8 mmol) in water (20 ml) was heated at 100° C. for 2 h. The mixture was allowed to cool to room temperature, the pH adjusted to 5 by the addition of concentrated hydrochloric acid and the resulting cream-coloured solid filtered and air dried. This solid was suspended in Dowtherm A (20 ml) and heated under reflux for 18 h. The reaction mixture was diluted with diethyl ether (150 ml) and filtered to remove solids. The filtrate was evaporated, the residue triturated with isohexane (150 ml) and the solid collected by filtration, giving 7-trifluoromethyl-pyrido[2,3-c]pyridazin-4-ol (0.53 g, 35%) as a white solid: $δ_H$ (400 MHz, DMSO) 7.89–7.93 (2H, m), 8.72 (1H, d, J8), 14.23 (1H, s).

The above product (50 mg, 0.23 mmol) was dissolved in the minimum amount of refluxing chlorobenzene. The mixture was allowed to cool to ambient temperature before phosphorus oxychloride (54 mg, 0.35 mmol) and pyridine (18 mg, 0.23 mmol) were added. This mixture was then heated under reflux for 1 h, cooled to ambient temperature and concentrated in vacuo. The black residue was diluted with water (10 ml), layered with ethyl acetate (10 ml) then the pH of the aqueous was adjusted to 8 by the addition of saturated sodium hydrogencarbonate solution. The aqueous phase was extracted with ethyl acetate (2×75 ml), the organics combined and washed with brine (30 ml), dried over anhydrous sodium sulphate, filtered and evaporated to give 4-chloro-7-trifluoromethylpyrido[2,3-c]pyridazine as a brown oil. This oil was used without further purification.

A mixture of the above product (54 mg, 0.23 mmol), 2'-fluoro-5'-(4,4,5,5-tetramethyl- [1,3,2]dioxaborolan-2-yl) biphenyl-2-carbonitrile (prepared as described in WO 02/074773) (150 mg, 0.46 mmol) and tetrakis(triphenylphosphine)palladium(0) (13 mg, 0.012 mmol) in 1,2-dimethoxyethane (4 ml) and 2N sodium carbonate solution (0.75 ml) was heated by microwave irradiation at 150° C. for 12.5 min. The mixture was allowed to cool to ambient temperature, diluted with water (200 ml) then extracted with ethyl acetate (2×75 ml). The combined organics were washed with brine, dried over anhydrous sodium sulphate, filtered and evaporated to give a black oil. This oil was purified by silica cartridge eluting with dichloromethane on a gradient of methanol (0–2%). Collecting appropriate fractions gave a purple solid. Trituration with diethyl ether (3 ml) and filtration gave the title compound (75 mg, 82%) as a yellow solid: $δ_H$ (360 MHz, CDCl$_3$) 7.54–7.76 (6H, m), 7.87 (1H, d, J8), 8.09 (1H, d, J9), 8.91 (1H, d, J9), 9.58 (1H, s); m/z (ES$^+$) 395 (M$^+$+H).

What is claimed is:

1. A compound of the formula I, or a pharmaceutically acceptable salt thereof:

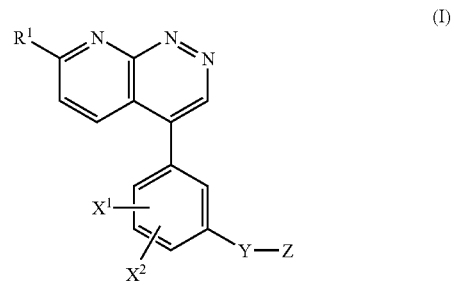

wherein:
$X^1$ represents hydrogen, halogen, $C_{1-6}$ alkyl, trifluoromethyl or $C_{1-6}$ alkoxy;
$X^2$ represents hydrogen or halogen;
Y represents a chemical bond, an oxygen atom, or a —NH— linkage;
Z represents an optionally substituted aryl or heteroaryl group;
$R^1$ represents hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$) alkyl, $C_{1-6}$ alkoxy($C_{1-6}$)alkyl, di($C_{1-6}$)alkoxy($C_{1-6}$) alkyl, cyano($C_{1-6}$)alkyl, $C_{2-6}$ alkoxycarbonyl($C_{1-6}$) alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl or —CR$^a$=NOR$^b$;
$R^a$ and $R^b$ independently represent hydrogen, or a heterocyclic group.

2. The compound of claim 1 of the formula IIA:

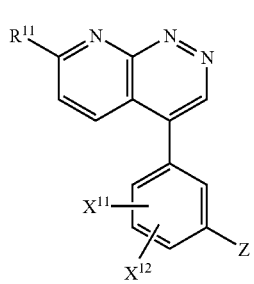

(IIA)

wherein:

X$^{11}$ represents hydrogen, fluoro, chloro, methyl, trifluoromethyl or methoxy;

X$^{12}$ represents hydrogen or fluoro;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, dihydroxy(C$_{1-6}$) alkyl, C$_{1-6}$ alkoxy(C$_{1-6}$)alkyl, di(C$_{1-6}$alkoxy(C$_{1-6}$alkyl, cyano(C$_{1-6}$)alkyl, C$_{2-6}$ alkoxycarbonyl(C$_{1-6}$)alkyl, C$_{3-7}$ cycloalkyl, heteroaryl, C$_{1-6}$ alkyl-heteroaryl, heteroaryl (C$_{1-6}$alkyl, halogen, cyano, trifluoromethyl, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl; and

R$^5$ hydrogen, C$_{1-6}$ alkyl, hydroxy(C$_{1-6}$)alkyl or di(C$_{1-6}$) alkylamino(C$_{1-6}$)alkyl.

3. The compound of claim 2 of the formula IIB:

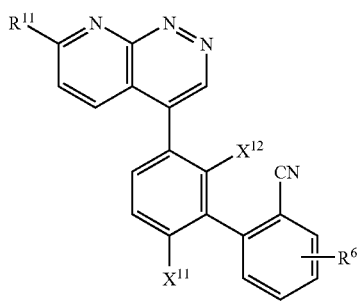

(IIB)

wherein R$^6$ represents hydrogen or fluoro.

4. The compound of claim 2 of the formula IIC:

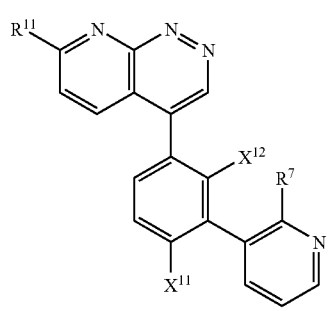

(IIC)

wherein R$^7$ represents hydrogen, fluoro, cyano or methyl.

5. The compound of claim 2 of the formula IID:

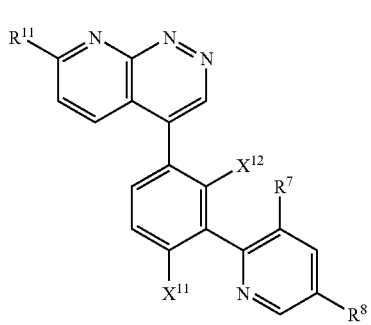

(IID)

wherein R$^8$ represents hydro or fluoro.

6. A compound which is 2'-fluoro 5'-(7-trifluoromethylpyrido[2,3-c]pyridazin-4-yl)biphenyl-2-carbonitrile, or a pharmaceutically acceptable salt thereof.

7. A pharmaceutically composition comprising the compound of claim 1, or a pharmaceutically acceptable salt thereof, and a pharmaceutically acceptable excipient.

8. A pharmaceutically composition comprising the compound of claim 6, or a pharmaceutically acceptable salt thereof, and a pharmaceutically acceptable excipient.

* * * * *